(12) United States Patent
Kim et al.

(10) Patent No.: US 10,376,530 B2
(45) Date of Patent: Aug. 13, 2019

(54) PHARMACEUTICAL COMPOSITION FOR PREVENTING OR TREATING GLEEVEC-RESISTANT LEUKEMIA CONTAINING GINSENOSIDE F1 OR GINSENOSIDE $R_g3$ AS AN ACTIVE INGREDIENT

(71) Applicant: INTELLIGENT SYNTHETIC BIOLOGY CENTER, Daejeon (KR)

(72) Inventors: Sun Chang Kim, Daejeon (KR); Hun Sik Kim, Seoul (KR)

(73) Assignee: Intelligent Synthetic Biology Center, Daejeon (KR)

( * ) Notice: Subject to any disclaimer, the term of this patent is extended or adjusted under 35 U.S.C. 154(b) by 0 days.

(21) Appl. No.: 15/511,637

(22) PCT Filed: May 4, 2016

(86) PCT No.: PCT/KR2016/004699
§ 371 (c)(1),
(2) Date: Mar. 15, 2017

(87) PCT Pub. No.: WO2016/178510
PCT Pub. Date: Nov. 10, 2016

(65) Prior Publication Data
US 2018/0071327 A1 Mar. 15, 2018

(30) Foreign Application Priority Data
May 6, 2015 (KR) ........................ 10-2015-0063390

(51) Int. Cl.
| | | |
|---|---|---|
| A61K 31/70 | (2006.01) | |
| A61P 35/02 | (2006.01) | |
| A61K 31/704 | (2006.01) | |
| A61K 45/06 | (2006.01) | |
| A61K 31/506 | (2006.01) | |
| A23L 33/125 | (2016.01) | |
| A61P 35/00 | (2006.01) | |

(52) U.S. Cl.
CPC .......... *A61K 31/704* (2013.01); *A23L 33/125* (2016.08); *A61K 31/506* (2013.01); *A61K 31/70* (2013.01); *A61K 45/06* (2013.01); *A61P 35/00* (2018.01); *A61P 35/02* (2018.01); *A23V 2002/00* (2013.01)

(58) Field of Classification Search
CPC .................................................... A61K 31/704
See application file for complete search history.

(56) References Cited

U.S. PATENT DOCUMENTS

2003/0158105 A1   8/2003   Sawyers et al.

FOREIGN PATENT DOCUMENTS

| CN | 102068477 | * | 5/2011 |
|---|---|---|---|
| JP | 2014-111629 | | 6/2014 |
| KR | 10-2011-0055833 | | 5/2011 |
| KR | 10-2014-0127985 | | 11/2014 |
| WO | WO 2004/056379 | | 7/2004 |
| WO | WO 2008-078203 | | 7/2008 |

OTHER PUBLICATIONS

Machine translation of CN 10206477. (Year: 2011).*
Caplus abstract of Wang, Y. et al "Experiment study on effect of ginsenoside Rg3 . . . " Zhongyaocai, vol. 34, No. 8, pp. 1270-1273. (Year: 2011).*
Peng, X. et al "Overexpression of P-glycoprotein induces acquired resistance . . . " Chin. J. Cancer, vol. 31, issue 31, pp. 115-118. (Year: 2012).*
Tung, N. et al "Dammarane-type saponins from the flower buds of Panax . . . " Bioorg. Med. Chem. Lett., vol. 20, pp. 309-314. (Year: 2010).*
Swords, R. et al "Nilotinib: optimal therapy for patients . . . " Drug Des. Devel. Ther., vol. 3, pp. 89-101. (Year: 2009).*
"Innatinib resistance in CML" Cancer Lett., vol. 274, pp. 1-9. (Year: 2009).*
"Drug transporters play a key role in the complex process . . . " Leukemia Res., vol. 39, pp. 355-360. (Year: 2015).*
Choi, C. -H. et al., "Reversal of P-glycoprotein-mediated multidrug resistance by protopanaxatriol ginsenosides from Korean red ginseng", Planta Medica, 69(3), 235-240, 2003.
Hasegawa, H. et al., "Reversal of daunomycin and vinblastine resistance in multidrug-resistant P388 leukemia in vitro through enhanced cytotoxicity by triterpenoids", Planta Medica, 61(5), 409-413, 1995.
Hou, Y. et al., "Ginseng Extract Enhances Anti-cancer Effect of Cytarabine on Human Acute Leukemia Cells", Advance Journal of Food Science and Technology, 7(3), 164-168, 2015.
Kim, S. -W. et al., "Reversal of P-glycoprotein-mediated multidrug resistance by ginsenoside Rg3", Biochemical Pharmacology, 65, 75-82, 2003.
Kwon, H. -Y et al., "Selective Toxicity of Ginsenoside Rg3 on Multidrug Resistant Cells by Membrane Fluidity Modulation", Archive of Pharmacal Research, 31(2), 171-177, 2008.

(Continued)

*Primary Examiner* — Leigh C Maier
(74) *Attorney, Agent, or Firm* — Parker Highlander PLLC

(57) ABSTRACT

The present invention relates to a pharmaceutical composition for preventing or treating Gleevec-resistant leukemia, containing, as an active ingredient, ginsenoside F1 or Rg3 which exhibits a preventive or therapeutic effect on Gleevec-resistant leukemia through enhancing cell killing activity of NK cells; a method for treating Gleevec-resistant leukemia comprising a step of administering the pharmaceutical composition; and a food composition for preventing or ameliorating Gleevec-resistant leukemia. Since the pharmaceutical composition of the present invention can effectively treat leukemia that exhibits resistance to conventional Gleevec, the pharmaceutical composition can be widely used for effective leukemia treatment.

2 Claims, 4 Drawing Sheets

(56) References Cited

OTHER PUBLICATIONS

Arunasree, Kalle M., et al. "Imatinib-resistant K562 cells are more sensitive to celecoxib, a selective COX-2 inhibitor: role of COX-2 and MDR-1." *Leukemia research* 32.6 (2008): 855-864.
Extended European Search Report issued in European Patent Application No. 16789616.6, dated Jan. 31, 2018.
Murphy et al., "Immunobiology", $7^{th}$ ed., published by Nankodo Co., Ltd., Japan, 2015, p. 412-413. English Abstract.
Murphy et al., "Immunobiology", $7^{th}$ ed., published by Nankodo Co., Ltd., Japan, 2015, p. 365-366. English Abstract.
Wang, T., and Z. Meng. "Experiment for immunity effects of ginsenoside $Rg_3$." *Journal-China Pharmaceutical University* 30 (1999): 133-135. English Abstract.
Yoo, Dae-Sung, et al. "Ginsenoside F1 modulates cellular responses of skin melanoma cells," *Journal of Ginseng Research* 35.1 (2011): 86-91.

\* cited by examiner

[FIG. 1]
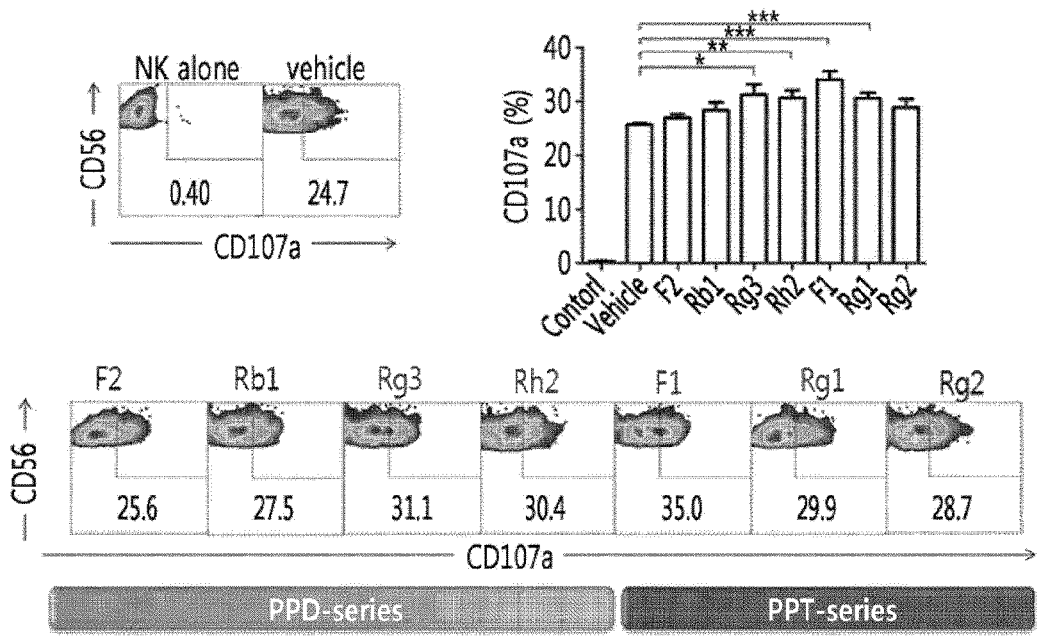
[FIG. 2]
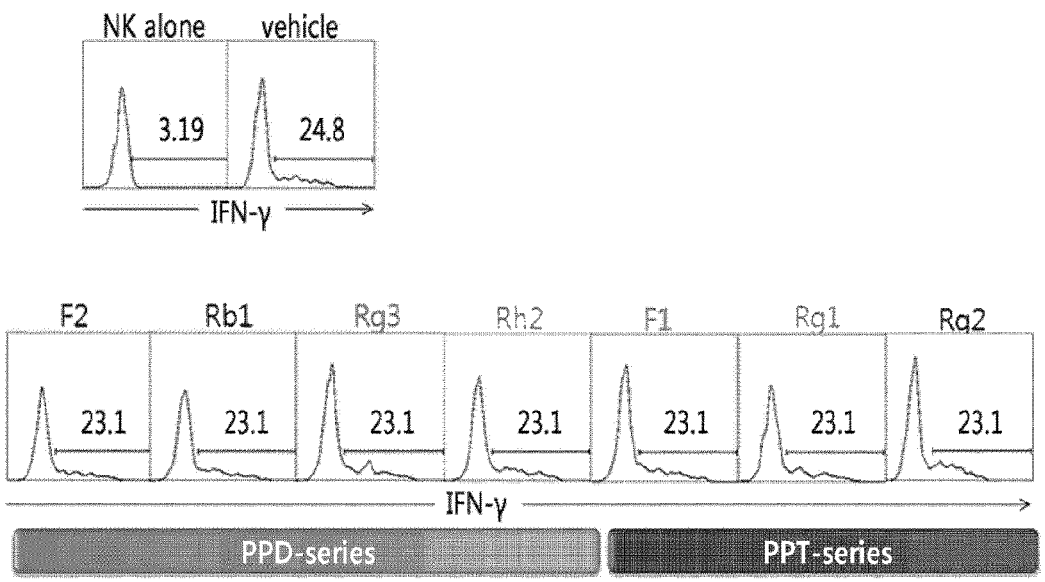

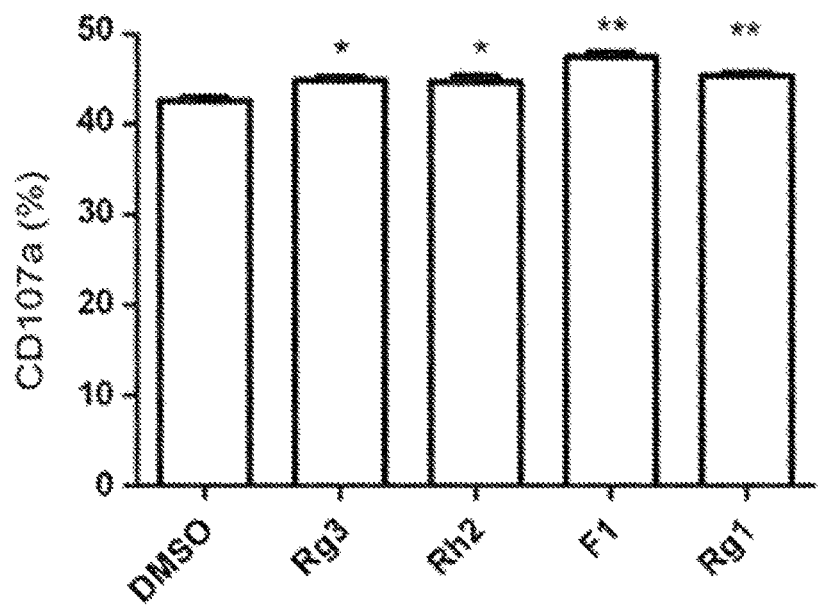
[FIG. 3]

[FIG. 4A]
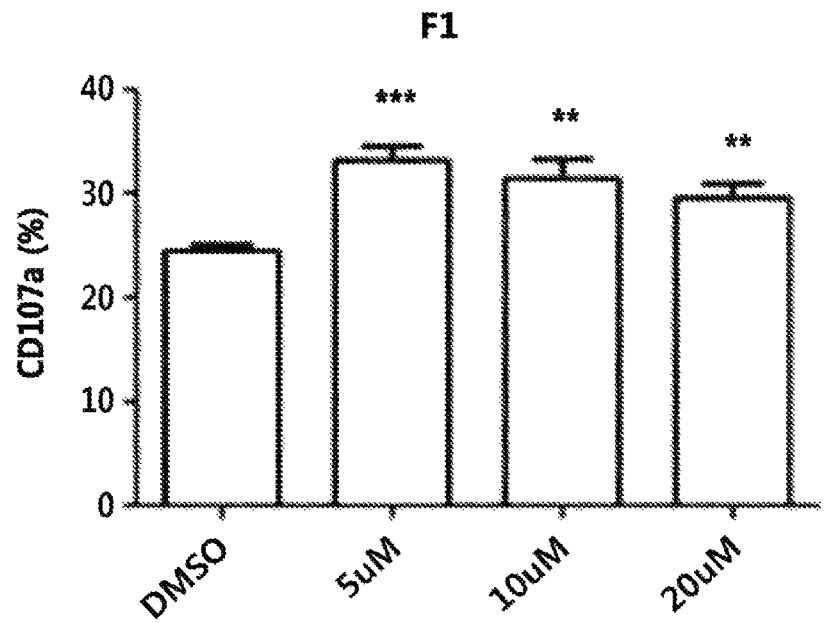
[FIG. 4B]
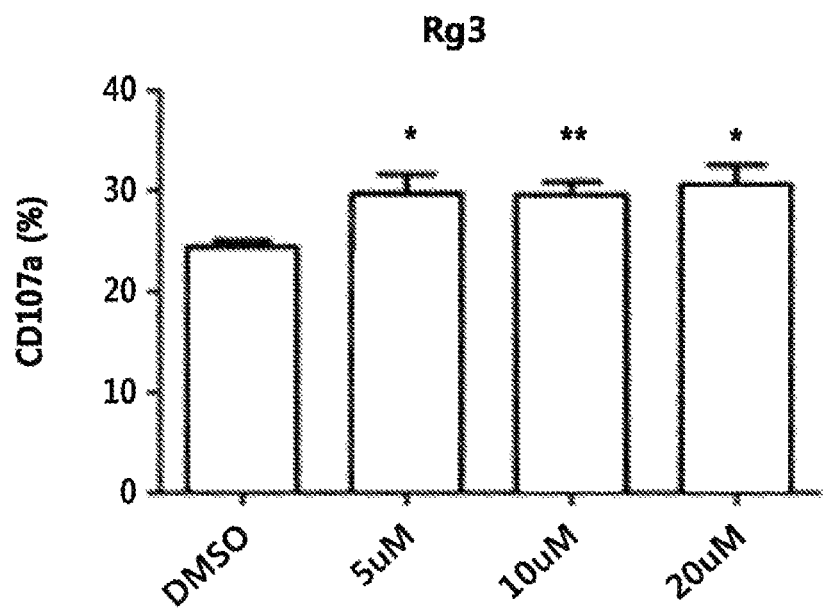

[FIG. 5A]
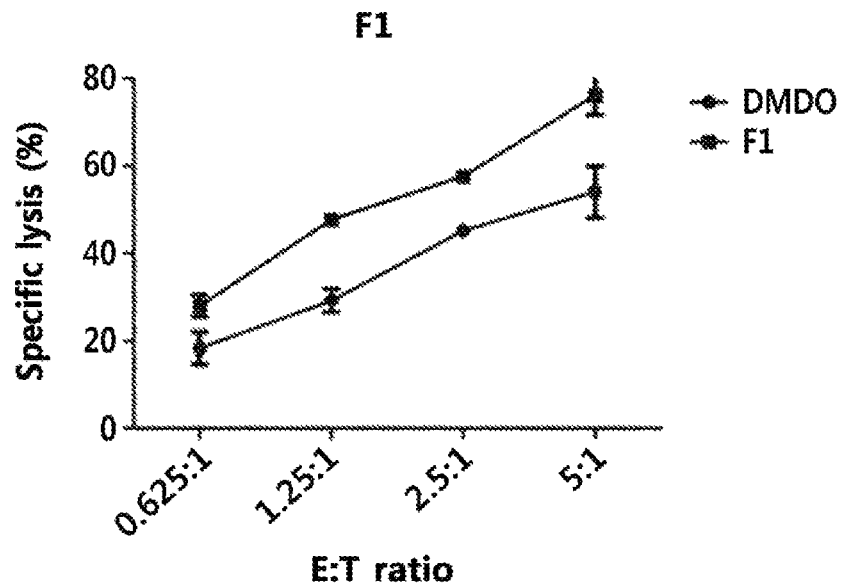
[FIG. 5B]
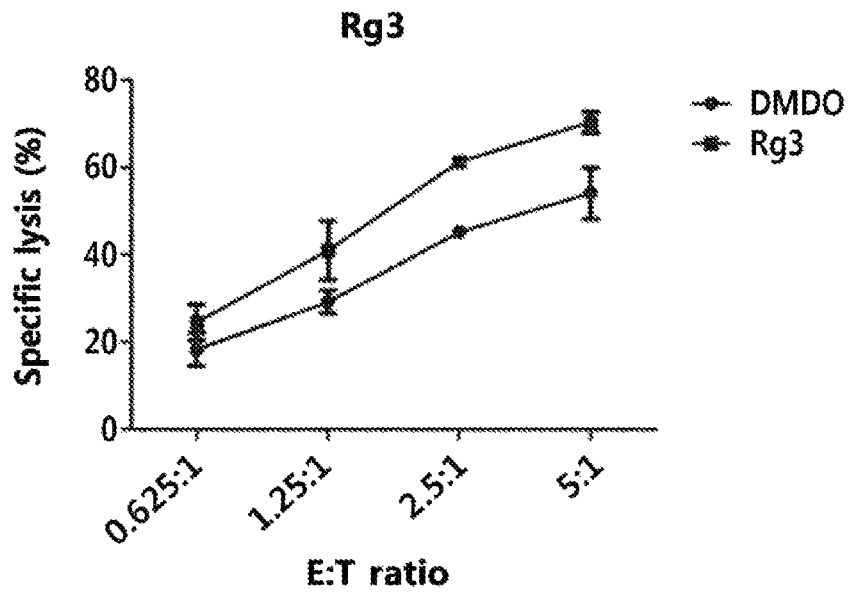

PHARMACEUTICAL COMPOSITION FOR PREVENTING OR TREATING GLEEVEC-RESISTANT LEUKEMIA CONTAINING GINSENOSIDE F1 OR GINSENOSIDE $R_g3$ AS AN ACTIVE INGREDIENT

This application is a national phase application under 35 U.S.C. § 371 of International Application No. PCT/KR2016/004699, filed May 4, 2016, which claims priority to Korean Application No. 10-2015-0063390, filed May 6, 2015, which are incorporated herein in their entirety.

TECHNICAL FIELD

The present invention relates to a pharmaceutical composition for preventing or treating Gleevec-resistant leukemia containing ginsenoside F1 or ginsenoside Rg3 as an active ingredient, and more specifically, to a pharmaceutical composition for preventing or treating Gleevec-resistant leukemia containing ginsenoside F1, ginsenoside Rg3, or a pharmaceutically acceptable salt thereof, which exhibits a preventive or therapeutic effect with respect to Gleevec-resistant leukemia, as an active ingredient, a method for treating Gleevec-resistant leukemia including administering the pharmaceutical composition, and a food composition for preventing or ameliorating Gleevec-resistant leukemia.

BACKGROUND ART

The mainstream methods for cancer treatment include surgery, chemotherapy, radiation therapy, etc. Among them, surgery and radiation therapy are local therapies effective only in the parts which are surgically removed or irradiated, whereas cancer drug therapy is a systemic therapy which affects the entire body. Most cancers are diseases that occur locally and metastasize systemically, and thus a mild level of systemic metastasis is already present unless the cancer is discovered at its extremely early stage. Therefore, it is quite normal to see a high rate of cancer recurrence despite effective local therapy. In this regard, cancer drug therapy, which is especially effective in the treatment of systemically-spread cancer, is used in combination with local therapy for most cancer treatments. In cancer treatment therapies, the administration of cancer drugs is an important therapy for removing extremely small cancer tissues which are difficult to observe by the naked eye or cancer cells which have been metastasized to other tissues from their primary site, after surgical removal of the cancer region. However, it is possible that some cancers may have resistance to particular cancer drugs, or cancer cells may acquire drug resistance during long-term administration of particular cancer drugs, thus making the cancer drugs ineffective.

Chronic myeloid leukemia (CML) is a malignant bone marrow tumor characterized by the uncontrolled increase in the production of bone marrow cell clones in bone marrow cells. According to a previous report with respect to CML by the International Agency for Research on Cancer (IARC), c-abl primary cancer gene on chromosome 9 moves to a new downstream location in the $2^{nd}$ exon of Bcr gene on chromosome 22, forms the Philadelphia chromosome (Ph), and expresses Bcr-Abl, a chimeric fusion protein, where the expressed fusion protein causes a series of inappropriate proliferation of blood-forming cells thus contributing to leukemic conversion. Gleevec, which is known as the most effective therapeutic agent for CML, is known to inhibit the growth of cells that express Bcr-Abl or induce apoptosis of the cells by acting through the competitive inhibition at the ATP-binding site, thereby exhibiting the effect of treating CML. However, since the disclosure that many CML patients show resistance to Gleevec (US Patent Application Publication No. 2003-0158105) was reported, there was a need for the development of a novel cancer drug capable of treating Gleevec-resistant CML, and thus studies are actively carried out for its development.

For example, WO Publication No. 2008-078203 discloses a pharmaceutical composition for treating Gleevec-resistant leukemia containing an extract of *Piper betle* leaves; Korean Patent Application Publication No. 2011-0055833 discloses a pharmaceutical composition for treating Gleevec-resistant leukemia containing 3-hydroxyflavone as an active ingredient; and Korean Patent Application Publication No. 2014-0127985 discloses a pharmaceutical composition for treating Gleevec-resistant leukemia containing an extract of yellow poplar cortex. Since these pharmaceutical compositions are mostly derived from natural products, they have an advantage in that they exhibit effects of treating Gleevec-resistant leukemia while being capable of minimizing their side-effects. However, these pharmaceutical compositions also have a problem in that they require long-term administration due to their poor therapeutic effects against Gleevec-resistant leukemia. Accordingly, there is a need for the development of a therapeutic agent which can exhibit excellent therapeutic effects for Gleevec-resistant leukemia with minimal side-effects.

DISCLOSURE

Technical Problem

The present inventors have made many efforts to develop a therapeutic agent capable of exhibiting excellent therapeutic effects for Gleevec-resistant leukemia while minimizing side-effects. As a result, the present inventors have found that F1 and Rg3, which are kinds of ginsenosides, have excellent therapeutic effects for Gleevec-resistant leukemia while being capable of minimizing side-effects, thereby completing the present invention.

Technical Solution

An object of the present invention is to provide a pharmaceutical composition for preventing or treating Gleevec-resistant leukemia containing ginsenoside F1, ginsenoside Rg3 (which are kinds of ginsenosides), or a pharmaceutically acceptable salt thereof.

Another object of the present invention is to provide a method for treating Gleevec-resistant leukemia, which includes administering the pharmaceutical composition.

A further object of the present invention is to provide a food composition for preventing or ameliorating Gleevec-resistant leukemia containing ginsenoside F1 or ginsenoside Rg3.

Advantageous Effects of the Invention

The pharmaceutical composition of the present invention can effectively treat leukemia which shows resistance to Gleevec and is thus expected to be widely used for the effective treatment of leukemia.

BRIEF DESCRIPTION OF DRAWINGS

FIG. 1 shows graphs illustrating the results of discovering ginsenosides that increased the level of CD107a when NK cells were treated on PBMC and graphs illustrating the results of flow cytometry analysis.

FIG. 2 shows graphs illustrating the change in the expression level of IFN-γ according to the treatment with 7 kinds of ginsenosides.

FIG. 3 shows a graph illustrating the effect of ginsenosides on the level of CD107a on NK cells, whose expression level was increased by reacting with mutants of KCL-22 cells (i.e., Gleevec-resistant leukemia cells).

FIG. 4A shows a graph illustrating the changes in the level of CD107a expressed on NK cells according to the treatment with different concentrations of ginsenoside F1.

FIG. 4B shows a graph illustrating the changes in the level of CD107a expressed on NK cells according to the treatment with different concentrations of ginsenoside Rg3.

FIG. 5A shows a graph illustrating the cell-killing activity of NK cells against mutants of KCL-22 cells, which were treated with ginsenoside F1.

FIG. 5B shows a graph illustrating the cell-killing activity of NK cells against mutants of KCL-22 cells, which were treated with ginsenoside Rg3.

BEST MODE

While performing various studies to develop therapeutic agents which can exhibit excellent therapeutic effects for Gleevec-resistant leukemia with minimal side-effects, the present inventors have paid attention to natural killer cells (NK cells). The NK cells are known to play a central role in the occurrence of various human diseases with respect to cancers and viral infectious diseases. Unlike other immune cells, the NK cells are known to immediately detect and remove cancer cells and virus-infected cells; control immune responses through the expression of an immune-stimulating factor such as IFN-γ; suppress occurrence, proliferation, and metastasis of cancer cells; and remove cancer stem cells which are associated with cancer drug-resistance and recurrence of cancer. The present inventors had hypothesized that the improvement of the cell-killing activity of NK cells may lead to the efficient removal of abnormal blood cancer cells in the blood which can induce Gleevec-resistant leukemia, and searched for the components capable of improving the activity of NK cells, and as a result, have drawn their attention to ginsenosides. Ginsenosides are components extracted from *ginseng* and their safeties are already known. Various studies have been performed with respect to their pharmacological activities, and some of the ginsenosides are known to exhibit excellent anticancer activities against various cancers. Accordingly, studies were focused on obtaining those components which exhibit therapeutic effects against Gleevec-resistant leukemia, among the ginsenosides. As a result, it was confirmed that some of the ginsenosides can improve the cell-killing activity of the NK cells in vivo and facilitate NK cell-mediated removal of Gleevec-resistant leukemia cells, thereby exhibiting anticancer activity against Gleevec-resistant leukemia through NK cells. In particular, when NK cells were treated with Rg3 (a kind of ginsenoside belonging to protopanaxadiol) or F1 (a kind of ginsenoside belonging to protopanaxatriol) and then incubated with Gleevec-resistant leukemia, Gleevec-resistant leukemia cells were effectively removed by NK cells, thus confirming the excellent anticancer activity against Gleevec-resistant leukemia through NK cells stimulated with Rg3 or F1.

As described above, ginsenoside F1 or ginsenoside Rg3 may be used as an active ingredient of a therapeutic agent for treating Gleevec-resistant leukemia. The therapeutic effects of ginsenoside F1 and ginsenoside Rg3 on Gleevec-resistant leukemia had not been known previously but identified first by the present inventors.

Accordingly, when the pharmaceutical composition provided in the present invention is administered to a subject with leukemia, ginsenoside F1 or ginsenoside Rg3 does not directly act on the mutated blood cells that can induce Gleevec-resistant leukemia but increases the cell-killing activity of NK cells and exhibit anticancer activity in an indirect manner to remove the mutated blood cancer cells, thus having an advantage in that the composition can exhibit excellent therapeutic effect in patients with Gleevec-resistant leukemia. Due to the advantage, the pharmaceutical composition provided in the present invention may be administered alone to a subject with Gleevec-resistant leukemia or may be administered in combination with other therapeutic agent(s)(e.g., imatinib, nilotinib, radotinib, ibrutinib, etc.) which exhibit a therapeutic effect against leukemia.

To achieve the above objects, an aspect of the present invention provides a pharmaceutical composition for preventing or treating Gleevec-resistant leukemia, containing F1, Rg3 (kinds of ginsenosides), or a pharmaceutically acceptable salt thereof.

As used herein, the term "ginsenoside F1", also called 20-O-β-D-glucopyranosyl-20(S)-protopanaxatriol, refers to a kind of PPT-series ginsenoside compounds represented by Formula 1. Ginsenoside F1 is known to be involved in the inhibition of cancer cell proliferation, increase in anticancer activity of cancer drugs, inhibition of allergies, and protection of human HaCaT keratinocytes from apoptosis by ultraviolet B (UVB) irradiation. However, the effect of ginsenoside F1 with respect to enhancing the cell-killing activity of natural killer cells had not been known.

[Formula 1]

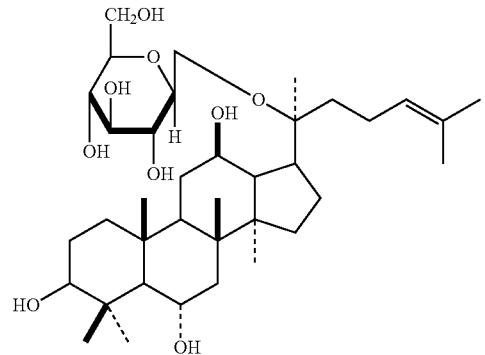

As used herein, the term "ginsenoside Rg3", also called 20(S)-protopanaxadiol-3-0-β-D-glucopyranosyl(1,2)-β-D-glucopyranoside, refers to a kind of PPD-series ginsenoside compounds represented by Formula 2. Ginsenoside Rg3 is known to exhibit especially excellent anticancer activity among various ginsenosides. In addition to the anticancer activity, ginsenoside Rg3 is also known to exhibit various pharmacological activities, such as neuroprotective activity, platelet aggregation inhibitory activity, antioxidant activity, anti-inflammatory activity, renal protective activity, etc. However, the effect of ginsenoside Rg3 with respect to enhancing the cell-killing activity of natural killer cells had not been known.

[Formula 2]

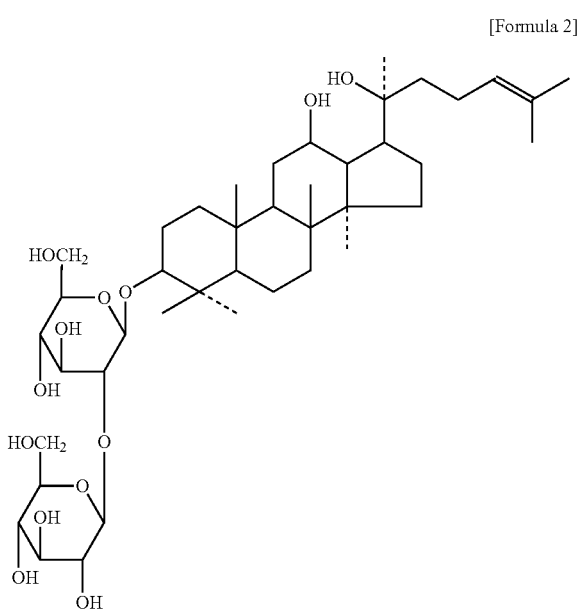

As used herein, the term "a pharmaceutically acceptable salt" refers to a salt which can be used pharmaceutically among the salts, where cations and anions are bound by electrostatic interaction. Conventionally, these salts may include metal salts, salts formed with organic bases, salts with inorganic acids, salts with organic acids, salts with basic or acidic amino acids, etc. For example, metal salts may include alkali metal salts (sodium salts, potassium salts, etc.), alkali earth metal salts (calcium salts, magnesium salts, barium salts, etc.), aluminum salts, etc.; salts with organic bases may include salts with triethylamine, pyridine, picoline, 2 6-lutidine, ethanolamine, diethanolamine, triethanolamine, cyclohexylamine, dicyclohexylamine, N,N-dibenzylethylenediamine, etc.; salts with inorganic acids may include salts with hydrochloric acid, hydrobromic acid, nitric acid, sulfuric acid, phosphoric acid, etc.; salts with organic acids may include salts with formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, etc.; salts with basic amino acids may include salts with arginine, lysine, ornithine, etc.; and salts with acidic amino acids may include salts with aspartic acid, glutamic acid, etc.

Specifically, preferable salts may include, in a case when the compound has an acidic functional group therein, inorganic salts such as an alkali metal salt (e.g., a sodium salt, a potassium salt, etc.) and an alkali earth metal salt (e.g., a calcium salt, a magnesium salt, a barium salt, etc.), and organic salts such as an ammonium salt; and in a case when the compound has a basic functional group therein, salts with an inorganic acid such as hydrochloric acid, hydrobromic acid, nitric acid, sulfuric acid, phosphoric acid, etc., and salts with an organic acid such as acetic acid, phthalic acid, fumaric acid, oxalic acid, tartaric acid, maleic acid, citric acid, succinic acid, methanesulfonic acid, p-toluenesulfonic acid, etc.

As used herein, the term "leukemia" refers to a disease in which leucocytes proliferate neoplastically. Leukemia may be classified into bone marrow leukemia and lymphoid leukemia according to the leucocytes from which the leukemia originates and may also be classified into acute leukemia and chronic leukemia according to its progress rate. The clinical features of leukemia appear in various forms according to the types of the disease and the characteristics of the invaded cells. For example, it is known that lymphoid leukemia occurs due to the mutation in the lymphoid blood cells, myeloid leukemia due to the mutation in the bone marrow blood cells, chronic myeloid leukemia due to the mutation in the bone marrow cells at a mature stage, and acute myeloid leukemia due to the mutation in the bone marrow mother cells which initiate the differentiation at a relatively early stage of homeopoiesis.

In the present invention, leukemia may be interpreted as referring to Gleevec-resistant leukemia, and Gleevec-resistant leukemia can be treated by the administration of the pharmaceutical composition provided in the present invention.

As used herein, the term "Gleevec-resistant leukemia" refers to leukemia that exhibits therapeutic resistance to Gleevec, which was developed as a therapeutic agent for the treatment of chronic myeloid leukemia (CML).

As described above, the pharmaceutical composition for preventing or treating Gleevec-resistant leukemia provided in the present invention contains ginsenoside F1 or ginsenoside Rg3, enhances the cell-killing activity of the NK cells in the body, and allows the NK cells with enhanced cell-killing activity to remove the mutated blood cancer cells, which can induce Gleevec-resistant leukemia. Therefore, the pharmaceutical composition can not only exhibit its therapeutic effect against Gleevec-resistant leukemia but also can be safely administered without side effects. Accordingly, the pharmaceutical composition provided in the present invention may be administered alone to a subject with Gleevec-resistant leukemia or administered in combination with other therapeutic agents (e.g., Gleevec (imatinib), nilotinib, radotinib, ibrutinib, etc.) having therapeutic effects against leukemia.

According to an exemplary embodiment of the present invention, a total of 15 different kinds of ginsenosides (C-K, F2, PPD, Rb1, Rb2, Rc, Rd, Rg3, Rh2, F1, PPT, Re, Rg1, Rg2, and Rh1) were screened to select ginsenosides capable of enhancing the cell-killing activity of the NK cells in the blood. As a result, 7 different kinds of ginsenosides (F2, Rb1, Rg3, Rh2, F1, Rg1, and Rg2) capable of enhancing the cell-killing activity were discovered (FIG. 1), and again 4 different kinds of ginsenosides (Rg3, Rh2, F1, and Rg1) capable of expressing immune-stimulating factor (IFN-γ) were discovered from the 7 different kinds of ginsenosides, and again 2 different kinds of ginsenosides (F1 and Rg3) capable of activating the NK cells (FIG. 3) and capable of activating the NK cells in a concentration-dependent manner (FIGS. 4A and 4B) were discovered. Subsequently, the effect of the 2 different kinds of ginsenosides on the cell-killing activity of NK cells was examined, and as a result, it was confirmed that the 2 different kinds of ginsenosides can increase the cell-killing activity of NK cells against Gleevec-resistant leukemia cells (FIGS. 5A and 5B).

The pharmaceutical composition of the present invention may further contain an appropriate carrier, excipient, or diluent conventionally used in the preparation of pharmaceutical compositions, and the carrier may be non-naturally occurring. Specifically, the pharmaceutical composition may be prepared for use in the form of oral formulations such as powders, granules, tablets, capsules, suspensions, emulsions, syrups, aerosols, etc.; formulations for external use; suppositories; and sterile injections, according to the conventional methods, respectively. In the present invention, the carrier, excipient, or diluent to be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. The formulations may be prepared using a diluent or excipient, such as a filler, an extender, a binder, a humectant, a disintegrant, a surfactant, etc. Solid formulations for oral administration may include tablets, pills, powders, granules, capsules, etc., and these solid formulations may be prepared by adding at least one excipient, e.g., starch, calcium carbonate, sucrose or lactose, gelatin, etc. Additionally, a lubricant, such as magnesium stearate, talc, etc., may be used, in addition to the simple excipient. Liquid formulations for oral administration may include suspensions, liquid medicines for internal use, emulsions, syrups, etc., and various excipients, such as humectants, sweeteners, fragrances, preservatives, etc., may be used, in addition to the simple diluents such as water and liquid paraffin. Formulations for parenteral administration may include sterile aqueous solutions, non-aqueous solvents, suspensions, emulsions, lyophilized formulations, and suppositories. Examples of the non-aqueous solvents and suspensions may include propylene glycol, polyethylene glycol, vegetable oils such as olive oil, an injectable ester such as ethyl oleate, etc. Examples of the bases for suppositories may include Witepsol, macrogol, Tween 61, cacao butter, laurinum, glycerogelatin, etc.

In an exemplary embodiment of the present invention, the amount of the formulation to be contained in the pharmaceutical composition may be in an amount of 0.0001 wt % to 50 wt %, and more preferably 0.01 wt % to 10 wt %, based on the total amount of the final composition, but is not limited thereto.

The composition of the present invention may be administered in a pharmaceutically effective amount. As used herein, the term "pharmaceutically effective amount" refers to an amount sufficient for the treatment of diseases at a reasonable benefit/risk ratio applicable to a medical treatment or prevention, and the level of the effective dose may be determined based on the factors including severity of illness, drug activity, a patient's age, body weight, health conditions, sex, drug sensitivity of a patient, administration time, administration route, excretion rate, and length of treatment of the composition used in the present invention, factors including drug(s) to be concurrently used in combination with the composition used in the present invention, and other factors well-known in the medical field. The pharmaceutical composition of the present invention may be administered as an individual therapeutic agent, in combination with other therapeutic agent(s), or sequentially or simultaneously with a conventional therapeutic agent(s), and may be administered once or multiple times. It is important to administer an amount to obtain the maximum effect with a minimum amount without adverse effects considering the factors described above.

The administration dose of the pharmaceutical composition of the present invention may be determined by one or ordinary skill in the art considering the purpose of use, severity of disease, a patient's age, body weight, sex, anamnesis of a patient, or a kind of material(s) to be used as an active ingredient, etc. For example, the pharmaceutical composition of the present invention may be administered in an amount of 10 mg/kg to 100 mg/kg, and more preferably 10 mg/kg to 30 mg/kg to a mammal including humans, and the frequency of administration of the pharmaceutical composition of the present invention may be administered 1 to 3 times daily or several times in divided doses a day, but is not particularly limited thereto.

To achieve the above object, in another aspect, the present invention provides a method for treating Gleevec-resistant leukemia including administering a pharmaceutically effective amount of the pharmaceutical composition to a subject with Gleevec-resistant leukemia. In particular, the pharmaceutical composition may be administered alone or in combination with another pharmaceutical composition (e.g., imatinib, nilotinib, radotinib, ibrutinib, etc.) for treating leukemia of a subject.

As used herein, the term "subject" refers to all kinds of animals including humans which have Gleevec-resistant leukemia. Gleevec-resistant leukemia can be treated by administering the composition of the present invention to a subject with the disease.

As used herein, the term "treatment" refers to all kinds of actions associated with the improvement or advantageous changes in symptoms of Gleevec-resistant leukemia by administering the pharmaceutical composition of the present invention.

As used herein, the term "administration" refers to introduction of a pharmaceutical composition of the present invention to a subject by any appropriate method, and the composition may be administered through various oral or parenteral routes as long as they enable the delivery of the composition to the target tissue.

With respect to the method of treating Gleevec-resistant leukemia according to the present invention, the pharmaceutical composition may be administered by any general route as long as it can deliver the composition to the target tissue. The pharmaceutical composition of the present invention may be administered intraperitoneally, intravenously, intramuscularly, subcutaneously, intradermally, orally, intranasally, intrapulmonarily, and intrarectally. Additionally, the pharmaceutical composition of the present invention may be administered by any device that can deliver the active ingredient to the target cells.

Another aspect of the present invention provides a food composition for preventing or ameliorating Gleevec-resistant leukemia containing F1 or Rg3, which is a kind of ginsenosides.

Since ginsenoside F1 and ginsenoside Rg3 are compounds derived from *ginseng* which has been used as food or medicine from the ancient times, they can be prepared to be eaten in the form of foods exhibiting the effect of preventing Gleevec-resistant leukemia or ameliorating Gleevec-resistant leukemia already occurred. In particular, although the amount of ginsenoside F1 or ginsenoside Rg3 is not particularly limited, they may be preferably contained in an amount of 0.001 wt % to 10 wt %, and more preferably 0.1 wt % to 1 wt %, relative to the total weight of a given food composition. When the food is a beverage, it may be contained in an amount of 1 g to 10 g, and preferably 2 g to 7 g, relative to 100 mL. Additionally, the composition may contain additional ingredients that are conventionally used in food compositions so as to improve smell, taste, vision, etc. For example, the composition may contain vitamins A, C, D, E, B1, B2, B6, B12, niacin, biotin, folate, pantothenic acid, etc. Additionally, the composition may also contain minerals such as Zn, Fe, Ca, Cr, Mg, Mn, Cu, etc. Additionally, the composition may also contain amino acids such as lysine, tryptophan, cysteine, valine, etc. Additionally, the composition may also contain food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclemate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount according to the food types.

Meanwhile, a health functional food for preventing or ameliorating Gleevec-resistant leukemia may be prepared using a food composition for preventing or ameliorating Gleevec-resistant leukemia containing ginsenoside F1 or ginsenoside Rg3.

In a specific embodiment, processed foods for preventing or ameliorating Gleevec-resistant leukemia may be prepared using the food composition. For example, a health functional food may be prepared in the form of confectioneries, beverages, alcohols, fermented foods, canned foods, milk-processed foods, meat-processed foods, or noodle-processed foods. In particular, confectioneries may include biscuits, pies, cakes, breads, candies, jellies, gums, cereals (meal substitutes such as grain flakes, etc.), etc. Examples of beverages may include drinking water, carbonated drinks, functional ion drinks, juices (e.g., apple, pear, grape, aloe, tangerine, peach, carrot, tomato juices, etc.), sweet rice drinks, etc. Examples of alcohols may include refined rice wine, whiskey, soju, beer, liquor, fruit wine, etc. Examples of fermented foods may include soy sauce, soybean paste, red pepper paste, etc. Examples of canned foods may include canned marine products (e.g., canned products of tuna, mackerel, pacific saury, conch, etc.), canned meat products (canned products of beef, pork, chicken, turkey, etc.), canned agricultural products (canned products of corn, peach, pineapple, etc.), etc. Examples of milk-processed products may include cheese, butter, yogurt, etc. Examples of meat-processed foods may include pork cutlet, beef cutlet, chicken cutlet, sausage, sweet-and-sour pork, nuggets, Neobiani, etc. Noodles such as sealing-packed wet noodles may be included. Additionally, the food composition may be used in retort foods, soups, etc.

As used herein, the term "functional food", being the same term as food for special health use (FoSHU), refers to a food with high medicinal and medical effects to efficiently exhibit a bioregulatory function in addition to a function of nutrient supply. The functional food may be prepared in various forms such as tablets, capsules, powders, granules, liquids, pills, etc., to obtain useful effects for preventing or ameliorating leukemia.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1: Discovery of Ginsenosides Capable of Improving Cell-Killing Activity of NK Cells To discover ginsenosides which can affect the cell-killing activity of NK cells, peripheral blood mononuclear cells (PBMC) separated from the blood were treated with 15 different kinds of (C-K, F2, PPD, Rb1, Rb2, Rc, Rd, Rg3, Rh2, F1, PPT, Re, Rg1, Rg2, and Rh1) ginsenosides, and then, the level of CD107a, which is a marker protein representing cell-killing activity and expressed on NK cells, was measured by flow cytometry (FIG. 1).

In particular, for the PBMC, those selected as follows were used. That is, the collected blood samples were transferred into Vacutainer Cell Preparation tubes (sodium heparin; BD Biosciences), centrifuged to recover a buffy coat, lymphocytes and monocyte band, and the recovered buffy coat was washed with PBS and applied to the human NK cell negative selection kit (Miltenyl Biotech) to isolate PBMC. The isolated PBMC was applied to flow cytometry analysis using anti-CD3 antibody, anti-CD16 antibody, and anti-CD56 antibody, and then those samples, in which the NK cells contained in the PBMC had a purity of 95% or higher, were used in the following Examples.

Additionally, the CD107a level was measured as follows. That is, the PBMC samples, in which the NK cells had a purity of 95% or higher, were treated with each ginsenoside, and then treated with target cells (K562 cells) to stimulate NK cells. Then, the NK cells were isolated by performing flow cytometry analysis using anti-CD3 antibody and anti-CD56 antibody, and the NK cells were immunostained using anti-CD107a antibody and the level of CD107a was measured.

FIG. 1 shows graphs illustrating the results of discovering ginsenosides that increased the level of CD107a on NK cells and graphs illustrating the results of flow cytometry. As illustrated in FIG. 1, it was confirmed that 7 different kinds of ginsenosides (F2, Rb1, Rg3, Rh2, F1, Rg1, and Rg2) were able to increase the level of CD107a expression on NK cells.

Example 2: Selection of Ginsenosides Capable of Enhancing the Expression of Immune-Stimulating Factor (IFN-γ) by NK Cells The 7 different kinds of ginsenosides discovered in Example 1 were treated and those ginsenosides which increased the expression level of the immune-stimulating factor (IFN-γ) by NK cells were selected (FIG. 2). In particular, the expression level of IFN-γ was measured as follows. That is, the PBMC samples isolated in Example 1 were treated with each ginsenoside, stimulated by treating with the equal number of target cells (mutants of KCL-22 cells), and then treated with Brefeldin A (GolgiPlug; BD Biosciences). Thereafter, a flow cytometry analysis was performed using fluochrome-conjugated anti-CD3 antibody and anti-CD56 antibody to identify NK cells present in PBMC, and then treated with Cytofix/Cytoperm (BD Biosicences) for perforation, and immunostained with fluochrome-conjugated anti-IFN-γ antibody to measure the intracellular level of IFN-γ(FIG. 2).

FIG. 2 shows graphs illustrating the change in the expression level of IFN-γ according to the treatment with 7 different kinds of ginsenosides. As illustrated in FIG. 2, it was confirmed that the expression level of IFN-γ was increased when treated with 4 different kinds of ginsenosides (Rg3, Rh2, F1, and Rg1) among the 7 different kinds of ginsenosides.

Example 3: Selection of Ginsenosides Capable of Enhancing the Level of CD107a on Primary NK Cells An attempt was made to select ginsenosides which induce the increase of the CD107a level on primary NK cells among the 4 different kinds of ginsenosides (Rg3, Rh2, F1, and Rg1) selected in Example 2.

Specifically, the NK cells isolated from the PBMC were activated by treating with the 4 different kinds of ginsenosides, then incubated with mutants of KCL-22 cells (i.e., Gleevec-resistant leukemia cells), and the level of CD107a on NK cells was measured and compared (FIG. 3). In particular, NK cells treated with DMSO, instead of ginsenosides, were used as a control group.

FIG. 3 shows graphs illustrating the effect of ginsenosides on the level of CD107a, whose expression level was increased on NK cells by reacting mutants of KCL-22 cells (i.e., Gleevec-resistant leukemia cells). As illustrated in FIG. 3, the level of CD107a was increased on DMSO-treated NK cells when reacted with the mutants of KCL-22 cells (i.e., Gleevec-resistant leukemia cells). Additionally, the level of CD107a was shown to be highest when treated with F1 among the ginsenosides in all experimental conditions, and Rg3 treatment showed the $2^{nd}$ highest CD107a level.

Example 4: Concentration-Dependent Effects of Ginsenoside F1 and Ginsenoside Rg3 on the Increase of CD107a Level on NK Cells NK cells isolated from PBMC were treated with ginsenoside F1 (which increases the selected CD107a level to the highest level) and Rg3 (which increases the selected CD107a level to the $2^{nd}$ highest level), selected from Example 3, at various concentrations (5 μM to 20 μM), and the change in the CD107a level was measured (FIGS. 4A and 4B). In particular, NK cells treated with DMSO, instead of ginsenosides, were used as a control group.

FIG. 4A shows a graph illustrating the changes in the level of CD107a expressed on NK cells according to the treated concentrations of ginsenoside F1; and FIG. 4B shows a graph illustrating the changes in the level of CD107a expressed on NK cells according to the treated concentrations of ginsenoside Rg3. As illustrated in FIGS. 4A and 4B, it was confirmed that both ginsenoside F1 and ginsenoside Rg3 were able to increase the expression levels of CD107a on NK cells in a concentration-dependent manner.

Accordingly, the analysis was interpreted such that ginsenoside F1 or ginsenoside Rg3 can promote the cell-killing activity of NK cells against Gleevec-resistant leukemia cells.

Example 5: Cell-Killing Activity of NK Cells According to Treatment with Ginsenoside F1 or Ginsenoside Rg3

The NK cells isolated in Example 1 was treated with ginsenoside F1 or ginsenoside Rg3, and incubated with target cells (Gleevec-resistant mutants of KCL-22 cells) labeled with an europium fluorescent dye at various E:T ratios (the ratio between the number of NK cells:the number of target cells=0.625:1, 1.25:1, 2.5:1, or 5:1), and thereby breaking down the target cells with the NK cells activated by the ginsenoside, and the europium fluorescent dye labeled to the target cells was released as a reaction solution. Upon completion of the reaction, the level of the europium fluorescent dye contained in the reaction solution was measured, and the cell-killing activity of the NK cells was compared (FIGS. 5A and 5B). In particular, NK cells treated with DMSO, instead of ginsenosides, were used as control group.

FIG. 5A shows a graph illustrating the cell-killing activity of NK cells, which were treated with ginsenoside F1, against Gleevec-resistant mutants of KCL-22 cells; and FIG. 5B shows a graph illustrating the cell-killing activity of NK cells, which were treated with ginsenoside Rg3, against mutants of KCL-22 cells. As illustrated in FIGS. 5A and 5B, it was confirmed that ginsenoside F1 or ginsenoside Rg3 was able to promote the cell-killing activity of NK cells against mutants of KCL-22 cells.

Summarizing the above, it was confirmed that ginsenoside F1 or ginsenoside Rg3 can enhance the cell-killing activity against Gleevec-resistant leukemia cells, by activating NK cells.

Accordingly, it was confirmed that ginsenoside F1 or ginsenoside Rg3 can be used as an active ingredient of a pharmaceutical composition for preventing or treating of Gleevec-resistant leukemia.

The invention claimed is:

1. A method for treating imatinib-resistant leukemia comprising administering a composition comprising ginsenoside F1 or a pharmaceutically acceptable salt thereof as the only active ingredient to a subject having or at risk of developing imatinib-resistant leukemia, wherein the leukemia is chronic myelogenous leukemia (CML) or acute lymphoblastic leukemia (ALL), wherein ginsenoside F1 improves the cell-killing activity of natural killer cells.

2. The method of claim 1, further comprising a pharmaceutically acceptable carrier, excipient, or diluent.

* * * * *